(12) United States Patent
O'Beirne et al.

(10) Patent No.: US 8,873,900 B2
(45) Date of Patent: Oct. 28, 2014

(54) BALLOON CATHETER WITH INTEGRATED OPTICAL SENSOR FOR DETERMINING BALLOON DIAMETER

(75) Inventors: Patricia O'Beirne, Galway (IE); Aram Jamous, Oranmore (IE); John Kelly, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 641 days.

(21) Appl. No.: 13/091,319

(22) Filed: Apr. 21, 2011

(65) Prior Publication Data
US 2012/0271339 A1   Oct. 25, 2012

(51) Int. Cl.
| G02B 6/00 | (2006.01) |
| A61M 29/00 | (2006.01) |
| A61M 25/10 | (2013.01) |
| G01L 1/24 | (2006.01) |

(52) U.S. Cl.
CPC .............. *A61M 25/104* (2013.01); *G01L 1/246* (2013.01); *A61M 2205/3306* (2013.01)
USPC ................................ 385/13; 385/12; 606/194

(58) Field of Classification Search
USPC ........... 385/115–121, 12–13; 606/20–26, 194
See application file for complete search history.

(56) References Cited

U.S. PATENT DOCUMENTS

| 5,171,299 | A | 12/1992 | Heitzmann et al. |
| 5,178,153 | A * | 1/1993 | Einzig ............................ 600/505 |
| 5,275,169 | A | 1/1994 | Afromowitz et al. |
| 5,399,854 | A | 3/1995 | Dunphy et al. |
| 5,500,180 | A | 3/1996 | Anderson |
| 7,004,911 | B1 * | 2/2006 | Tu et al. .......................... 600/549 |
| 7,153,299 | B1 * | 12/2006 | Tu et al. .......................... 606/15 |
| 7,189,227 | B2 | 3/2007 | Lafontaine |
| 7,297,154 | B2 * | 11/2007 | Tu et al. .......................... 607/88 |
| 7,336,862 | B1 | 2/2008 | Young et al. |
| 7,418,169 | B2 * | 8/2008 | Tearney et al. .................. 385/25 |
| 7,421,162 | B2 | 9/2008 | McCarthy |
| 8,145,018 | B2 * | 3/2012 | Shishkov et al. ............... 385/33 |
| 2005/0075704 | A1 * | 4/2005 | Tu et al. .......................... 607/88 |
| 2005/0131289 | A1 * | 6/2005 | Aharoni et al. ............... 600/407 |
| 2007/0078500 | A1 * | 4/2007 | Ryan et al. ...................... 607/88 |
| 2007/0188855 | A1 * | 8/2007 | Shishkov et al. ............. 359/362 |
| 2007/0232893 | A1 * | 10/2007 | Tanioka ........................ 600/407 |
| 2008/0097288 | A1 * | 4/2008 | Levin et al. ...................... 604/66 |
| 2008/0114254 | A1 * | 5/2008 | Matcovitch et al. ........... 600/463 |
| 2009/0123111 | A1 * | 5/2009 | Udd ................................ 385/13 |
| 2009/0137952 | A1 * | 5/2009 | Ramamurthy et al. ..... 604/95.01 |
| 2009/0143686 | A1 * | 6/2009 | Onimura et al. .............. 600/477 |
| 2009/0177090 | A1 * | 7/2009 | Grunwald et al. ............. 600/454 |
| 2009/0234282 | A1 | 9/2009 | McAndrew et al. |
| 2009/0262361 | A1 * | 10/2009 | Tanioka et al. ................ 356/479 |
| 2010/0056904 | A1 * | 3/2010 | Saunders et al. .............. 600/424 |

(Continued)

*Primary Examiner* — Ryan Lepisto
*Assistant Examiner* — Guy Anderson

(57) ABSTRACT

An apparatus and method for determining an expanded diameter of a catheter balloon. An optical sensor includes an elongated optical fiber with at least one diffraction grating formed in a core of a distal portion thereof. The fiber distal portion is coupled to the inflatable balloon. Broadband light is transmitted to the diffraction grating by an optical interrogator. A portion of the light is reflected from the diffraction grating and is received by a wavelength detector. The wavelength of the reflected portion of light is dependent on the strain applied to the diffraction grating. The wavelength detector determines the strain in the balloon and correlates the strain to the diameter of the balloon.

17 Claims, 4 Drawing Sheets

(56) References Cited

U.S. PATENT DOCUMENTS

| | | | |
|---|---|---|---|
| 2010/0076437 A1* | 3/2010 | Tilson et al. | 606/63 |
| 2010/0094328 A1* | 4/2010 | O'dea et al. | 606/192 |
| 2010/0168836 A1* | 7/2010 | Kassab | 623/1.11 |
| 2010/0210937 A1* | 8/2010 | Tearney et al. | 600/424 |
| 2010/0241178 A1* | 9/2010 | Tilson et al. | 606/86 R |
| 2010/0286678 A1* | 11/2010 | Weber et al. | 606/21 |
| 2013/0211261 A1* | 8/2013 | Wang et al. | 600/476 |

* cited by examiner

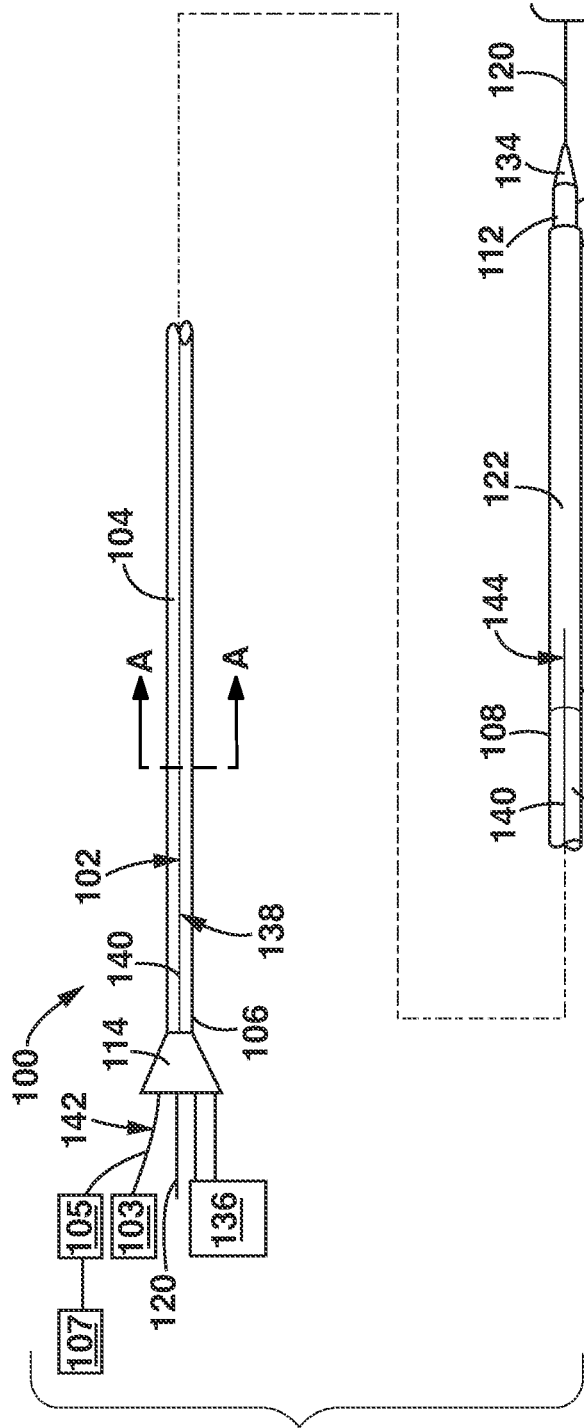
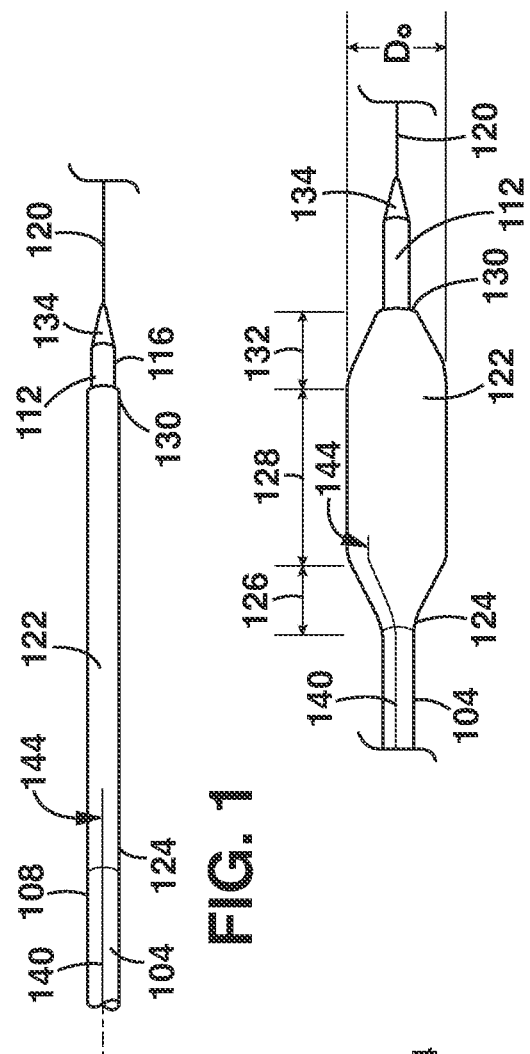
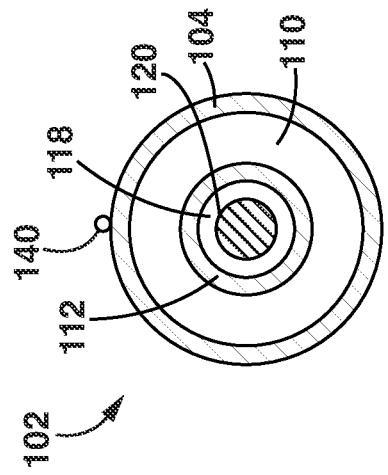

BALLOON CATHETER WITH INTEGRATED OPTICAL SENSOR FOR DETERMINING BALLOON DIAMETER

FIELD OF THE INVENTION

In general, the invention relates to balloon catheters and more particularly, the invention relates to an optical sensor integrated into a balloon of a balloon catheter for determining a strain in the balloon during inflation and a system for correlating a diameter of the balloon based on the strain.

BACKGROUND OF THE INVENTION

Cardiovascular disease, including atherosclerosis, is the leading cause of death in the United States. One method for treating atherosclerosis and other forms of arterial lumen narrowing is percutaneous transluminal angioplasty, commonly referred to as "angioplasty" or "PTA," or "PTCA" when performed in the coronary arteries. The objective in angioplasty is to restore adequate blood flow through the affected artery, which may be accomplished by inflating a balloon of a balloon catheter within the narrowed lumen of the artery to dilate the vessel. Typically, inflation of the balloon is accomplished by supplying a pressurized fluid through an inflation lumen in the catheter which is connected to an inflation apparatus located outside of the patient's body. Similarly, applying suction to the inflation lumen collapses the balloon to its minimum dimension for initial placement of the balloon catheter within or removal from the target blood vessel.

A wide variety of angioplasty catheter designs and constructions are available. Typically, the catheter balloon is constructed of a thermoplastic elastomer (TPE) or other polymer configured to produce a nominal or labeled balloon diameter at a standard inflation pressure of six atmospheres. Because arteries differ in size, most balloon dilatation catheters are available in stepped dilation diameters ranging from approximately 1.5 millimeter to 4.0 millimeter in increments of 0.5 millimeter, or in the case of noncompliant balloons, in increments as small as 0.25 millimeter. After locating the stenosis in an artery or vessel utilizing a procedure such as an angiogram, the physician gauges the size of the affected vessel as accurately as possible and selects the corresponding balloon size to effectively open the lesion.

Dilatation balloons may be classified as being compliant, noncompliant or semi-compliant. Compliant angioplasty balloons are characterized by the balloon's ability to radially expand beyond its nominal diameter in response to increasing inflation pressure. Such balloons can be said to follow a stress-strain curve obtained by plotting balloon diameter versus inflation pressure. Noncompliant angioplasty balloons are characterized by a nearly flat stress-strain curve illustrating that the balloon diameter expands very little over the range of usable inflation pressures. It has been found that the optimal size of a dilatation balloon is about 0.9 to about 1.3 the size of the vessel being treated. See Nichols et al., *Importance of Balloon Size in Coronary Angioplasty*, J. American College of Cardiology, Vol. 13, 1094 (1989). If an undersized balloon is used, there is a high incidence of significant residual stenosis and a greater need for subsequent dilatation procedures. However, if an oversized balloon is used, there is an increased chance of coronary dissection. Therefore, physicians desire to use a balloon which will closely approximate the size of the occluded vessel or obstructed cavity being treated. Thus, when increased inflation pressures are required to open a resistant stenosis, physicians keep in mind that a compliant balloon will also be increasing in diameter. However, compliant balloons typically can suffer from some degree of plastic deformation during inflation such that, upon subsequent inflations, the balloon will achieve diameters greater than the diameters originally obtained at any given pressure.

Semi-compliant balloons have been developed that, as compared to compliant balloons, offer a reduced degree of radial expansion beyond their nominal diameter in response to increasing inflation pressure. Such balloons also resist plastic deformation during inflation such that the balloon diameter will follow a stress-strain curve even during repeated inflations. See U.S. Pat. No. 5,500,180. Thus, for several reasons, as a dilatation balloon expands in situ, it is desirable for the physician to accurately monitor the balloon diameter, but the only means available are by visual approximation of the balloon shown on a magnified x-ray image or by observing the pressure indicated on a balloon inflation device and trying to make a correlation between the indicated pressure and the actual balloon diameter.

In addition to balloon angioplasty procedures, stent prostheses are implanted within body lumens to provide artificial radial support to dilated, collapsing, weakened, and/or stenosed passageways, such as blood vessels of the body. Stent prostheses are typically constructed of a metal or polymer and are generally a hollow cylindrical shape. When a balloon-expandable stent is to be implanted, a balloon catheter carrying the stent mounted on its balloon is advanced to the target site, such as a stenosis. The balloon and accompanying stent are positioned at the location of the stenosis, and the balloon is inflated to radially expand and thereby implant the stent. As the balloon expands, it physically forces the stent to radially expand such that the outside surface of the stent comes into contact with the vessel wall. Thereafter, the balloon is deflated and the balloon catheter is withdrawn from the patient, leaving the stent in the expanded or deployed configuration. One criterion for successful stent deployment is apposition of the stent against the vessel wall, since any regions of the stent that protrude into the lumen may cause turbulent blood flow, which in turn may lead to acute thrombosis and arterial blockage. By "apposition" or "wall apposition" herein it is meant that at least the outer surface of the deployed stent is fully positioned against, i.e., makes contact with, the vessel wall. Proper stent apposition against the vessel wall is obtained by expanding the stent with a balloon inflated to the correct diameter.

Thus, it is desirable during both angioplasty and stent implantation procedures to accurately achieve the proper inflated diameter of the catheter balloon, and it is desirable for the physician to monitor the balloon diameter during balloon inflation to insure that the balloon is not under-inflated or over-inflated. Accordingly, there is a need for an apparatus and method that will effectively communicate real time balloon diameters to a physician during inflation of a catheter balloon. It is an object hereof to provide a system that is capable of determining and displaying an in vivo balloon diameter dimension during balloon inflation.

BRIEF SUMMARY OF THE INVENTION

Embodiments hereof relate to an apparatus for determining an expanded diameter of a balloon of a balloon catheter. A fiber Bragg grating (FBG) sensor includes at least one diffraction grating formed on a distal portion of an elongated waveguide or optical fiber. The diffraction grating is coupled to the inflatable balloon. A wavelength detector is coupled to a proximal end of the optical fiber. The wavelength detector is operable to receive a reflected portion of light from the diffraction grating, determine the strain in the balloon from the reflected portion of light, and correlate the strain to a dimension of an expanded diameter of the balloon.

Embodiments hereof also relate to a method for determining an expanded diameter of a balloon of a balloon catheter. The balloon catheter includes a FBG sensor coupled to the balloon. A FGB sensor includes at least one diffraction grating formed on a distal portion of an elongated optical fiber. The balloon of the balloon catheter is percutaneously positioned at a treatment site and the balloon is inflated. As the balloon radially expands, light from a broadband source is transmitted to the diffraction grating. A portion of light that is reflected from the diffraction grating is received at a wavelength detector, which determines the strain in the balloon from the reflected portion of light and correlates the strain to a dimension of the expanded diameter of the balloon.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a side view of a balloon catheter in accordance with an embodiment hereof, wherein the balloon is in an unexpanded configuration.

FIG. 1A is a cross-sectional view taken along line A-A of FIG. 1.

FIG. 2 is a side view of a distal portion of the balloon catheter of FIG. 1, wherein the balloon is in an expanded configuration.

DETAILED DESCRIPTION OF THE INVENTION

Figure 3A:
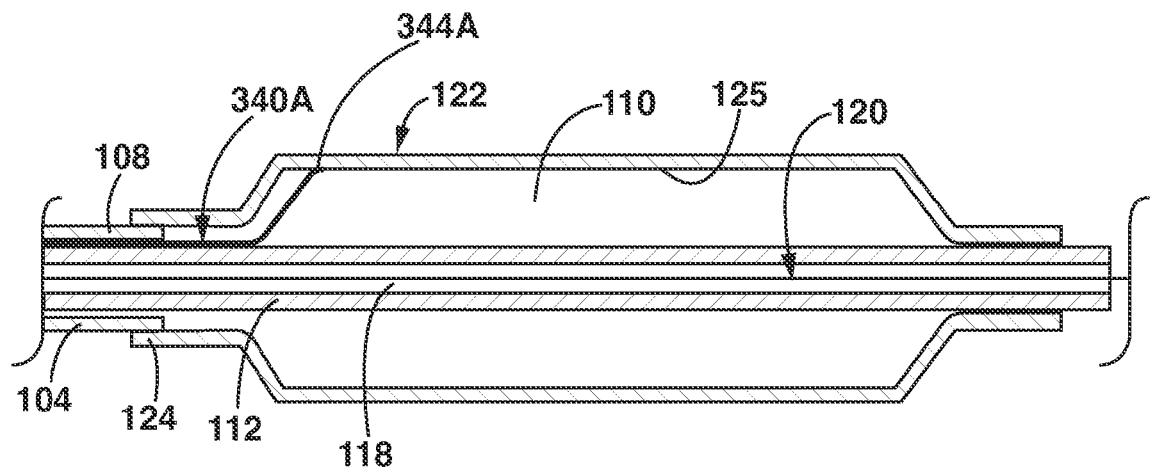
FIG. 3A is a side view of a distal portion of a balloon catheter in accordance with another embodiment hereof, wherein an optical fiber is coupled to an inside surface of a balloon which is shown in an expanded configuration.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of blood vessels such as the coronary, renal and other peripheral arteries, the invention may also be used in any other body passageways where it is deemed useful. Furthermore, there is no intention to be bound by any expressed or implied theory presented in the preceding technical field, background, brief summary or the following detailed description.

Embodiments hereof relate to a method of determining and displaying a balloon diameter using an optical strain gauge or sensor during inflation. The optical sensor for determining strain is a fiber Bragg grating (FBG) sensor that includes a diffraction grating formed in a short section of optical fiber. A wavelength detector correlates the strain in the balloon material into a diameter dimension of the expanding or expanded balloon. Although balloon catheters may be supplied to a user with a chart illustrating pressure measurements verses balloon diameter, direct sensing of strain is expected to be a more reliable and accurate indication of balloon diameter because the strain is sensed in vivo. For sensing strain in the balloon material in vivo, optical strain gauges in accordance with embodiments hereof are preferable over electronic strain gauges because optical strain gauges do not produce and are immune to electromagnetic interference, optical strain gauges produce low magnetic field interactions, and optical strain gauges match well with polymer materials. FBG sensors are particularly advantageous for sensing strain in the balloon material in vivo because they have a low profile such that they may be incorporated onto or into a catheter without significantly increasing the profile of the device.

More particularly, FIGS. 1, 1A, and 2 depict a catheter system 100 for determining balloon diameter according to an embodiment hereof. Catheter system 100 includes a balloon catheter 102 having an inflatable balloon 122 at its distal end, an optical sensor 138, an optical interrogator 103, and wavelength detector 105. Balloon 122 is shown in an unexpanded or delivery configuration in FIG. 1 and is shown in an expanded or inflated configuration in FIG. 2. In the embodiment shown in FIGS. 1, 1A and 2, balloon catheter 102 has an over-the-wire (OTW) catheter configuration with an inner guidewire shaft 112 that defines a guidewire lumen 118 extending substantially the entire length of the catheter for accommodating a guidewire 120. More particularly, catheter 102 includes a tubular component or outer shaft 104 having a proximal end 106 that extends out of the patient and is coupled to a hub 114 and a distal end 108 coupled to a proximal end 124 of balloon 122. A distal end 130 of balloon 122 is coupled to guidewire shaft 112. Guidewire shaft 112 has a proximal end (not shown) coupled to hub 114 and a distal end 116 terminating distally of balloon 122. Distal end 116 may be coupled to a tapered distal catheter tip 134 that defines a distal guidewire port. In an embodiment, guidewire shaft 112 may be a flexible tube of a polymeric material, such as, e.g., polyethylene tubing.

In the coaxial catheter construction of the illustrated embodiment, guidewire shaft 112 extends within outer shaft 104 such that an annular inflation lumen 110 is defined between an inner surface of outer shaft 104 and an outer surface of guidewire shaft 112. Other types of catheter construction are also amendable to the invention, such as, without limitation thereto, a catheter shaft formed by multi-lumen profile extrusion. In another embodiment, catheter 102 may be modified to be of a rapid exchange (RX) catheter configuration without departing from the scope of the present invention such that guidewire shaft 112 extends within only the distal portion of catheter 102 incorporating a distal portion of inflation lumen 110.

Inflation lumen 110 extends between proximal and distal ends 106, 108 of outer catheter shaft 104 to allow inflation fluid received through hub 114 to be delivered to balloon 122. As would be understood by one of ordinary skill in the art of balloon catheter design, hub 114 provides a luer hub or other type of fitting that may be connected to a source of inflation fluid 136 and may be of another construction or configuration without departing from the scope of the present invention. In embodiments hereof, catheter 102 may be used in balloon angioplasty procedures, as well as may form the basis of a stent delivery system, a graft delivery system, and/or a drug delivery system.

Balloon 122 includes a tapered proximal neck 126 and a tapered distal neck 132, with a working portion or length 128 extending between proximal neck 126 and distal neck 132. The working length 128 has an inflated outer diameter $D_O$ for contacting a vessel wall of a treatment site. Proximal neck 126 of balloon 122 is joined to distal end 108 of outer shaft 104 and distal neck 132 of balloon 122 is joined to guidewire shaft 112. Proximal and distal necks 126, 132 of balloon 122 may be joined to outer catheter shaft 104 and guidewire shaft 114, respectively, in any conventional manner known to one of skill in the art of balloon catheter construction, such as by laser welding, adhesives, heat fusing, or ultrasonic welding.

Optical sensor 138 is a fiber Bragg grating sensor that includes a distributed Bragg reflector or diffraction grating 450 (see FIG. 4) formed in a distal portion of an elongated optical fiber 140. The FGB sensor may be of the type described in U.S. Pat. No. 5,399,854 to Dunphy et al., U.S. Pat. No. 7,336,862 to Young et al., and U.S. Pat. No. 7,421,162 to McCarthy et al., each of which is incorporated by reference herein in its entirety. As will be described in more detail herein, the diffraction grating of a FBG sensor is a reflective element that reflects particular wavelengths of light and transmits all others. Diffraction grating 450 reflects a certain wavelength of light, whereby the wavelength of the reflected light is dependent on the strain in the optical fiber. Optical fiber 140 extends the entire length of catheter 102 with a proximal portion 142 extending out of the patient and optically coupled to an optical interrogator 103 and a distal portion 144 which is attached or otherwise coupled to an outer surface of balloon 122 as shown in FIGS. 1 and 2. Distal portion 144 includes diffraction grating 450 and is secured to balloon 122 in any suitable manner known to one of skill in the art of balloon catheter construction such as via an adhesive. Optical fiber 140 may be adhered along the outside surface of outer shaft 104 with an adhesive or other mechanical method at various places along the length of catheter 102 in order to prevent undesired movement of optical fiber 140 during tracking of the catheter through the vasculature. In another embodiment shown in FIG. 3A, optical fiber 340A may extend within catheter 102 and distal end 344A of optical fiber 340A may be attached to an inner surface 125 of balloon 122. More particularly, optical fiber 340A extends within annular inflation lumen 110 defined between outer shaft 104 and inner guidewire shaft 112. As such, optical fiber 340A is protected within catheter 102 during tracking of the catheter through the vasculature.

Figure 3B:
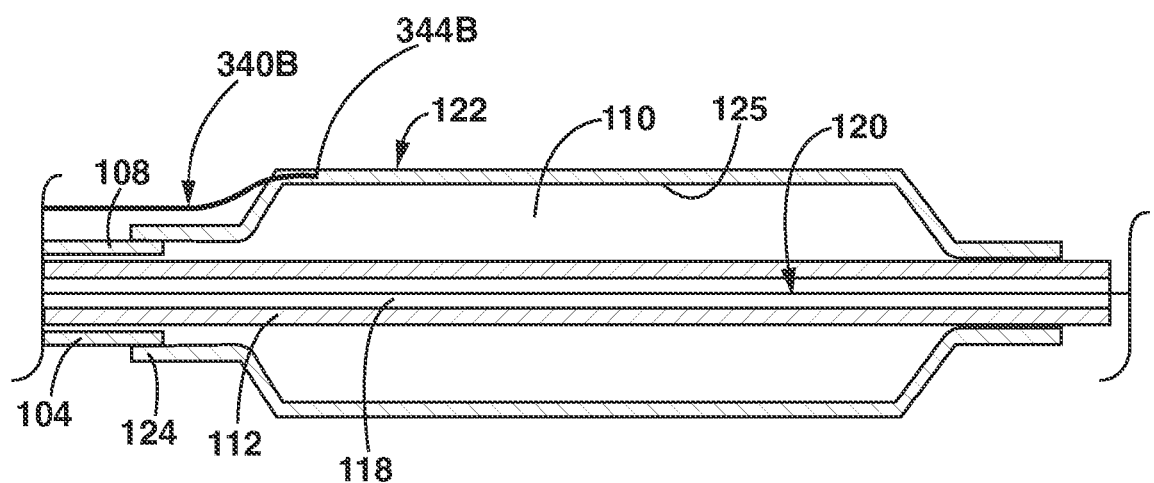
FIG. 3B is a side view of a distal portion of a balloon catheter in accordance with another embodiment hereof, wherein an optical fiber is embedded within material that forms a balloon which is shown in an expanded configuration.

In yet another embodiment shown in FIG. 3B, distal end 344B of optical fiber 340B is embedded into the material of balloon 122. One way to fabricate this structure is to form balloon 122 in two layers with fiber distal end 344B encapsulated between the two layers. An inner tubular balloon parison can be disposed inside an outer tubular balloon parison with fiber distal end 344B interposed between the inner and outer parisons. The assembly can then be placed in a conventional balloon forming machine and stretch blow molded to form balloon 122 with fiber 340B extending therefrom.

Figure 4:
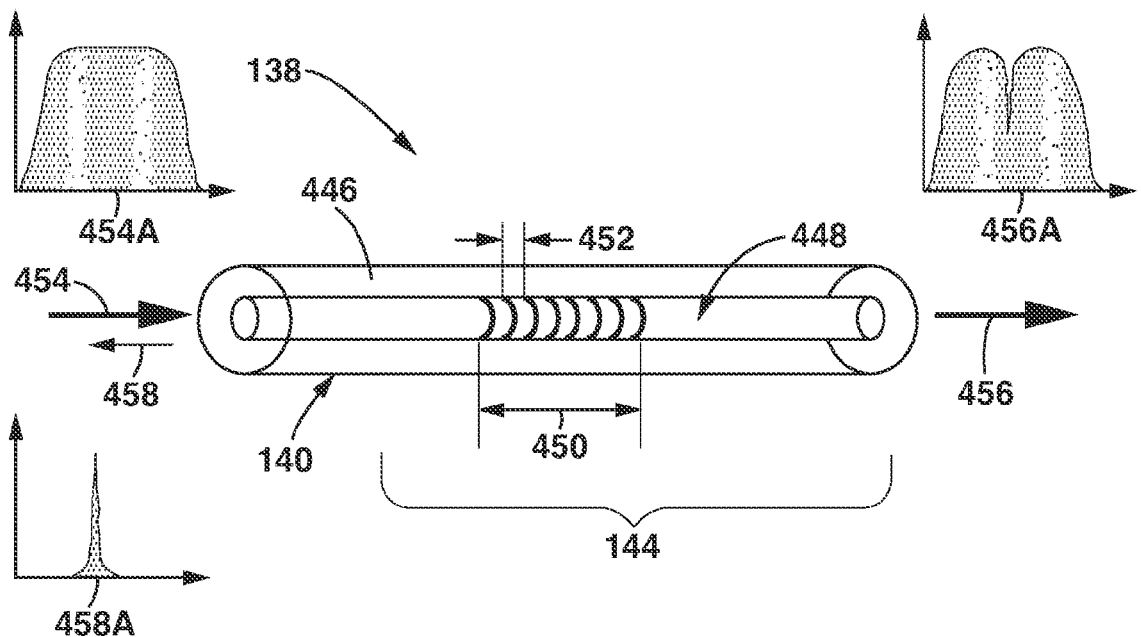
FIG. 4 is a schematic illustration of the operation of a known type of fiber Bragg grating sensor for use in embodiments hereof.

FIG. 4 illustrates the operation of a known FBG optical sensor 138 for measuring material strain. Optical fiber 140 includes a core 448 and a cladding 446 disposed thereover. Cladding 446 is pure glass ($SiO_2$) and core 448 has a higher refraction index caused by germanium doping. In one embodiment, core 448 is between 4 and 9 μm in diameter and cladding 446 is approximately 125 μm in diameter. Diffraction grating 450 is integrally formed on core 448 at or near distal portion 144 of optical fiber 140 by photolithographically writing or inscribing periodic variations of refractive index on core 448 using an intense ultraviolet source such as a laser. The period of grating 450 is typically 250 to 500 nm and the overall grating length may be between 0.5 and 1.0 mm. Optical interrogator 103 emits light 454, which has a wavelength represented by a graphical image 454A. Typical output wavelengths are centered around 850 nm or 1500 nm. Examples of commercially available optical interrogators that may be suitable for use herein include model 850-55-Python-4 by Technobis Fibre Technologies or model LC-GBMP by L.C. Pegasus Corporation of New Jersey, U.S.A. or model sm230 by Micron Optics, Inc. of Atlanta, Ga., U.S.A. In one embodiment, optical interrogator 103 may emit light through the optical fiber 140 at regular predetermined intervals in order to continuously monitor the diameter of balloon 122. For example, optical interrogator 103 may emit light 454 at an exemplary and non-limiting rate of 10 Hz. An interrogator may also emit light continuously and sample the reflected light intermittently at frequencies up to 20 kHz. Transmitted light 454 travels through optical fiber 140 via glass core 448 until it reaches and enters diffraction grating 450. The difference in refraction indexes between core 448 and cladding 446 causes light 454 to propagate only within core 448. Due to the periodic changes in refraction, grating 450 transmits a portion of light 456 having a wavelength represented by a graphical image 456A and reflects a portion of light 458 having a reflected or Bragg wavelength represented by a graphical image 458A. The reflected portion of light 458 is transmitted back through core 448 of optical fiber 140 to a wavelength detector 105. The Bragg wavelength at which the portion of light 458 is reflected is a function of the spacing or period 452 between inscriptions of diffraction grating 450. When strain occurs in balloon 122, diffraction grating 450 is stretched and period 452 increases. The increase of period 452 shifts the peak of the Bragg wavelength. Accordingly, as strain is applied to optical sensor 138, the Bragg wavelength of the reflected portion of light 458 shifts and the shift is proportional to the strain in optical fiber 140 and is therefore indicative of the strain in balloon 122. As balloon 122 expands, wavelength detector 105 utilizes the movement or shift in the Bragg wavelength of the reflected portion of light 458 in order to determine the strain within the material of balloon 122 during inflation. A wavelength detector 105 then correlates the strain into a diameter of balloon 122. Wavelength detector 105 may be coupled to a display 107 (see FIG. 1) in order to display the determined balloon diameter to the user. The format of display 107 includes but is not limited to a numerical readout of balloon diameter, a visual or pictorial illustration of balloon diameter, or other suitable display formats for communicating the diameter of the expanding balloon to a user.

Wavelength detector 105 may be a general-purpose or specific-purpose processing device or microcontroller and may be associated with a memory device (not shown) for storing data and/or instructions. The memory device can be any type of storage device or computer-readable medium, such as random access memory ("RAM") or read-only memory ("ROM"). The memory device stores logical instructions, commands, and/or code executed by wavelength detector 105. In another embodiment, logical instructions, commands, and/or code can be implemented in hardware and incorporated in wavelength detector 105 using discrete logic circuitry, an application specific integrated circuit ("ASIC"), a programmable gate array ("PGA"), a field programmable gate array ("FPGA"), etc., or any combination thereof. In yet another embodiment, logical instructions, commands, and/or code can be implemented in both hardware in wavelength detector 105 and software/firmware stored in the memory. Instrumentation for coupling optical fiber 140 to wavelength detector 105 may include one or more devices commonly used in optical fiber communication systems for demultiplexing an optical signal, such as a detection fiber (not shown), an optical coupler (not shown), a focusing/collimating lens (not shown), a charge coupled device array (not shown), and/or an analog-to-digital converter (not shown). In general, data acquisition and analysis of the optical parameters are well known to one of ordinary skill in the art. Further, although described as separate external devices, it would be understood by one of ordinary skill in the art that in one embodiment wavelength detector 105 and optical interrogator 103 may be combined in a single integral device.

Wavelength detector 105 typically utilizes an algorithm to determine the strain in balloon 122 from the reflected portion of light 458. In one embodiment, wavelength detector 105 utilizes a lookup table or an algorithm in order to correlate the strain to a diameter dimension of balloon 122. The relationship between strain and expanded diameter is dependent upon the parameters of the material of balloon 122, and wavelength detector 105 may store the material properties such as a strain parameter for one or more commonly used balloon materials. It is expected that the relationship between strain and diameter can be readily developed for any given balloon material and a corresponding algorithm downloaded into wavelength detector 105 such that the user may select or input the appropriate type of balloon material into wavelength detector 105 prior to the medical procedure.

In another embodiment, the material properties including a strain parameter of balloon 122 may be stored in an external memory device that serves as an input for wavelength detector 105. For example, the material properties of balloon 122 may be stored in a semiconductor chip that is embedded into or otherwise coupled to the catheter hub. The semiconductor chip is of standard construction and can be obtained from Alien Inc. or Matrix, Inc. which are two of many chip manufacturers in the semiconductor chip industry. Semiconductor chips may contain the material properties of balloon 122 as well as other pertinent information about a catheter such as model/serial number, manufacturing information and instructions for use.

Depending on the construction of a particular fiber Bragg grating sensor, the sensor is capable of sensing a limited and predetermined range of strain values within a sensing or working range thereof. Therefore, distal portion 144 must be mounted on balloon 122 such that the amount of strain occurring within the balloon material falls within the sensing range of FBG sensor 138. In the embodiments depicted within FIGS. 1, 1A, 2, 3A, and 3B, FBG sensor 138 is mounted parallel with a longitudinal axis of balloon 122 and is utilized for sensing strain occurring in the longitudinal or axial direction of the balloon, which may be correlated to an outer balloon diameter via wavelength detector 105 as described above. During expansion, balloon 122 typically encounters much less strain in the longitudinal direction than in the circumferential direction.

Figure 5:
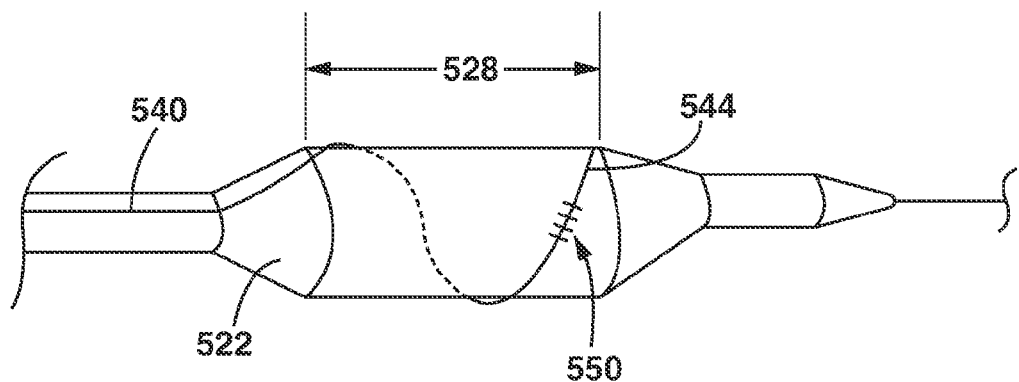
FIG. 5 is a side view of a distal portion of a balloon catheter in accordance with another embodiment hereof, wherein an optical fiber helically extends along an expanded balloon for sensing strain in the balloon.

In another embodiment, however, the fiber Bragg grating sensor may be mounted around the balloon in such a way as to be usable for measuring a combination of circumferential and longitudinal components of the strain in the balloon. Although balloon 122 typically encounters more strain in the circumferential direction than in the longitudinal direction, the combination of circumferential and longitudinal components of the strain values may still fall within the working or sensing range of a FBG sensor. As illustrated in FIG. 5, a distal portion 544 of optical fiber 540 extends helically around working portion 528 of balloon 522 and a diffraction grating 550 is positioned along the working portion 528 of the balloon. In the illustrative example, optical fiber 540 is mounted in a single helical wrap around the full length of balloon working portion 528. Typical balloons for blood vessel dilatation or stent deployment have a working portion length that is several times the inflated balloon diameter. When an optical fiber having a single helix is incorporated into balloons of such proportions, the angle formed between the fiber helix and the axis of the balloon is below 45 degrees, perhaps in a range of 20-30 degrees. The fiber helix angle is preferably low enough to avoid bending damage to the optical fiber when the balloon is deflated and wrapped around the catheter shaft. To minimize bending of the optical fiber, balloon wings may be wrapped with a twist that corresponds to the fiber helix. The algorithm utilized by wavelength detector 105 for a balloon having a helical optical fiber is expected to compensate for the fact that the FBG sensor is measuring a combination of longitudinal and circumferential components of balloon strain. The algorithm is expected to be determined, in part, by the angle at which the FBG sensor is positioned on the balloon.

An alternative embodiment may include a single optical fiber that has more than a single helical wrap around the balloon, and such an embodiment may include partial helical wraps of the fiber. More than one FBG sensor may be placed along a single optical fiber and multiplexed optically for measuring strain in more than one location of the balloon. In another embodiment, a plurality of parallel optical fibers may be helically wrapped around the balloon in multifilar fashion such as bifilar, trifilar, etc., each optical fiber having at least one fiber Bragg grating sensor. Using one of the above embodiments, multiple diffraction gratings may be positioned along the working portion of the balloon in order to monitor balloon diameter variation between the proximal end of the balloon and the distal end of the balloon and ensure symmetrical expansion of the balloon.

Outer shaft 104 may be formed of a polymeric material, non-exhaustive examples of which include polyethylene, polyethylene block amide copolymer (PEBA), polyamide and/or combinations thereof, either laminated, blended or co-extruded. Optionally, outer shaft 104 or some portion thereof may be formed as a composite having a reinforcement material incorporated within a polymeric body in order to enhance strength and/or flexibility. Suitable reinforcement layers include braiding, wire mesh layers, embedded axial wires, embedded helical or circumferential wires, and the like. In one embodiment, for example, at least a proximal portion of outer catheter shaft 104 may be formed from a reinforced polymeric tube.

Balloon 122 may be a semi-complaint angioplasty balloon formed from any suitable material for an inflatable medical balloon that is relatively elastic and deformable. Non-exhaustive examples of materials for balloon 122 include polymers such as polyethylene, PEBA, polyethylene terephthalate (PET), polyamide, and polyurethane, copolymers or blends thereof. In one embodiment, balloon 122 is a relatively elastic thermoplastic elastomer (TPE) material. In another embodiment, balloon 122 is a "no-fold" or "zero-fold" balloon formed from polyurethane, which means that the balloon material is not folded prior to inflation but instead has a generally cylindrical or tubular shape in the unexpanded configuration. The zero-fold balloon may be utilized in consecutive inflations or deployments, and may have different consecutive deployment diameters such that a user does not have to use multiple balloons with different deployment diameters. Further details regarding no-fold balloon technology are described in U.S. Patent Appl. Publ. No. 2009/0234282 to McAndrew et al., herein incorporated by reference in its entirety.

Figure 6:
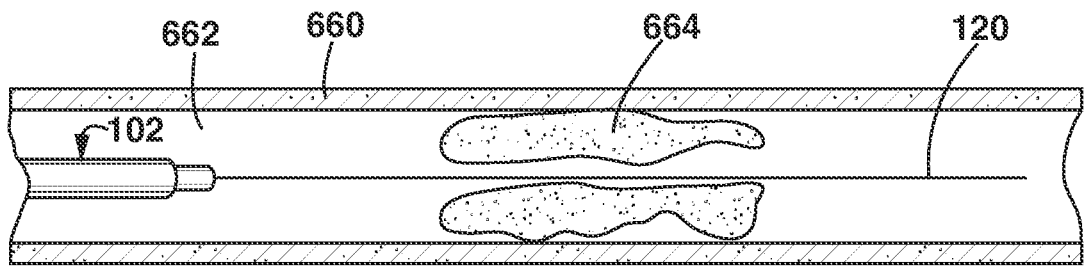
FIGS. 6-9 illustrate the steps of a method of determining balloon diameter according to an embodiment hereof.
Figure 7:
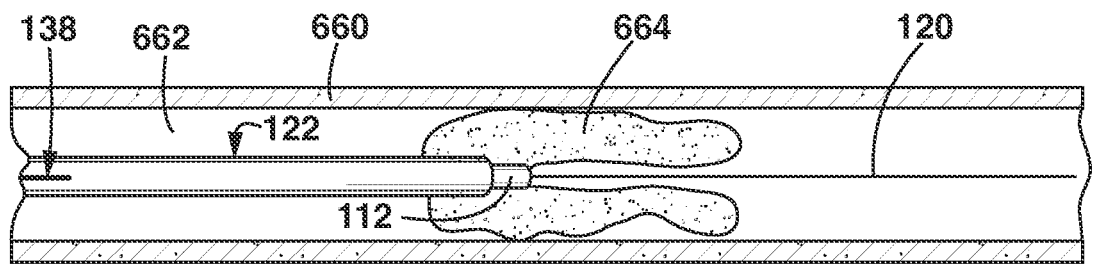
Figure 8:
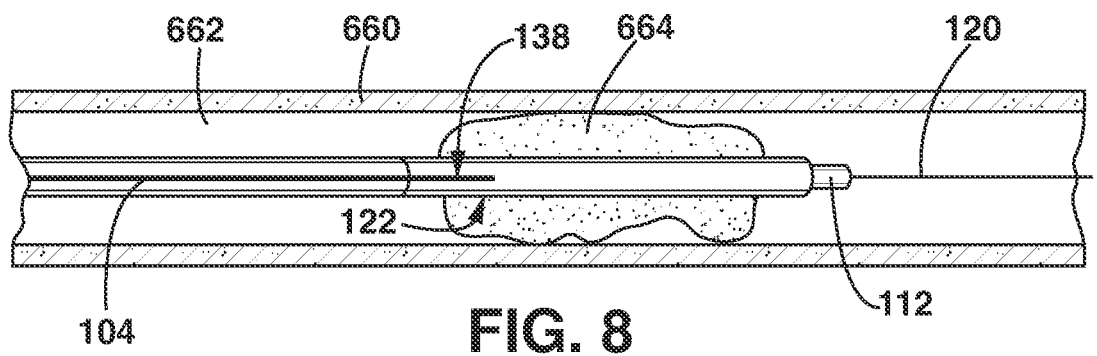

FIGS. 6-9 illustrate the steps of a method of monitoring balloon diameter in vivo during a medical procedure according to an embodiment hereof. Although described in relation a balloon angioplasty procedure, it should be understood that the methods and apparatus described herein may be used for any medical procedure which utilizes balloon inflation including but not limited to a stenting procedure, a graft procedure, and a drug delivery procedure. Typically, a guiding catheter is first inserted through an incision (not shown) and into a femoral artery of a patient. For example, the Seldinger technique may be utilized for percutaneously introducing the guiding catheter. A guidewire 120 may be introduced and maneuvered through the vasculature to a treatment site, which in this instance is a stenotic lesion 664 within lumen 662 of vessel 660 as shown in FIG. 6, and catheter 102 may be subsequently advanced thereover to the treatment site, or alternatively guidewire 120 and catheter 102 may be simultaneously tracked to lesion 664. As shown in FIG. 7, the catheter 102 is advanced until the distal end of catheter 102 is pushed into lesion 664. Catheter 102 is proximally advanced until balloon 122 successfully crosses lesion 664 to become longitudinally centered there within, as shown in FIG. 8.

Figure 9:
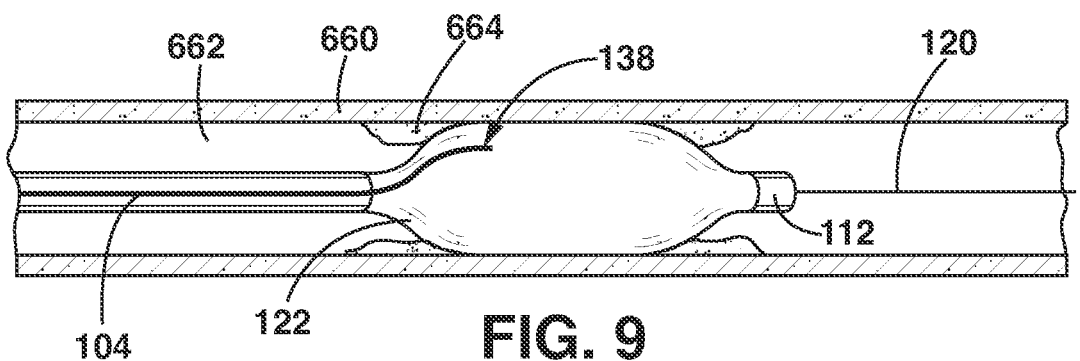

Once balloon 122 is positioned within the lesion, inflation fluid is introduced such that balloon 122 begins to radially expand. Balloon 122 will radially expand to its fully inflated configuration to dilate lesion 664 and thereby enlarge lumen 662 of vessel 660 at the lesion, as shown in FIG. 9. As the balloon expands, optical sensor 138 is utilized to monitor the outer diameter of balloon 122. As described above, optical interrogator 103 (not shown in FIGS. 6-9) emits broadband light and measures the reflected portion of the light, which is indicative of the strain in optical sensor 138 and is therefore indicative of the strain in balloon 122. The reflected portion of light is transmitted back to wavelength detector 105, which determines the strain in balloon 122 and correlates the strain to an expanded diameter of balloon 122. Wavelength detector 105 then displays the balloon diameter to the user via display 107. In an embodiment, as the inflation fluid pressure increases to between 12 atm and 15 atm, the working length 128 of balloon 122 will reach an expanded outer diameter between 1.20 mm and 1.40 mm. Via display 107, the user is notified when balloon 122 has reached its nominal diameter and apposition against the vessel wall may be presumed. Vessel apposition is of particular importance when catheter 102 forms the basis of a stent or graft delivery system, since it is important that no regions of the stent protrude into the body lumen. If the balloon is expanded beyond its nominal diameter, it is expected that a clinician will find it useful to compare the real time compliance of the balloon in vivo to previously stored information regarding unconstrained balloon compliance. Such a comparison, which may be shown graphically on display 107, may provide insight into the elasticity or rigidity of the vessel being treated, and thereby assist the clinician in avoiding vessel dissection Once the angioplasty procedure is completed, inflation fluid is withdrawn in order to deflate balloon 122. Upon deflation, balloon 122 may form wings or folds of material around catheter 102 and catheter 102 may be retracted from the patient. If desired, another interventional catheter such as a balloon catheter having a larger balloon or a stent delivery system may be delivered over indwelling guidewire 120 to lesion 664 in order to perform additional therapeutic procedures.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A catheter system comprising:
an elongate catheter having an inflatable balloon disposed at its distal end;
an optical fiber strain sensor including an elongate optical fiber with a diffraction fiber distal portion defined by at least one diffraction grating formed in a core of a distal portion of the optical fiber, wherein the diffraction fiber distal portion is coupled to the inflatable balloon; and
a wavelength detector coupled to a proximal end of the optical fiber, wherein the wavelength detector is configured to receive a reflected portion of light from the diffraction grating, to determine the strain in the balloon from the reflected portion of light, and to correlate the determined strain to a diameter of the balloon.

2. The system of claim 1, further comprising:
a semiconductor chip coupled to a hub of the catheter, wherein the semiconductor chip includes a strain parameter of the balloon that serves as an input for the wavelength detector.

3. The system of claim 1, wherein the diffraction fiber distal portion is coupled to one of an exterior surface and an interior surface of the inflatable balloon.

4. The system of claim 1, wherein the diffraction fiber distal portion is embedded within a wall of the inflatable balloon.

5. The system of claim 1, wherein the diffraction fiber distal portion is mounted parallel with a longitudinal axis of the balloon and a spectral shift of the reflected portion of light corresponds to a longitudinal strain in the balloon.

6. The system of claim 1, wherein the diffraction fiber distal portion is wrapped at least partially helically around the balloon and a spectral shift of the reflected portion of light corresponds to a combination of longitudinal and circumferential strain in the balloon.

7. The system of claim 6, wherein the diffraction fiber distal portion includes multiple diffraction gratings formed therein.

8. The system of claim 1, further comprising:
an optical interrogator coupled to a proximal end of the optical fiber, wherein the optical interrogator is operable to transmit ultraviolet light through the fiber to the at least one diffraction grating; and
a display coupled to the wavelength detector, wherein the display provides numerical readouts of the diameter of the balloon.

9. The system of claim 1, wherein the optical fiber strain sensor is a fiber Bragg grating sensor disposed in the core of the distal portion of the optical fiber.

10. A method for determining an expanded diameter of a catheter balloon, the method comprising the steps of:
percutaneously positioning an inflatable balloon of a catheter at a treatment site, wherein the catheter includes a fiber Bragg grating (FBG) sensor affixed to the inflatable balloon, the FBG sensor being disposed in the core of a distal portion of an elongate optical fiber;
inflating the balloon such that the balloon radially expands;
transmitting broadband light through the fiber to the FBG sensor;
receiving from the FBG sensor a reflected portion of the transmitted light;
determining a strain in the balloon from the reflected portion of the transmitted light; and
correlating the determined strain to the diameter of the balloon.

11. The method of claim 10, further comprising:
displaying the correlated balloon diameter.

12. The method of claim 10, wherein the fiber distal portion is coupled to one of an exterior surface and an interior surface of the inflatable balloon.

13. The method of claim 10, wherein the fiber distal portion is embedded within a wall of the inflatable balloon.

14. The method of claim 10, wherein the fiber distal portion is mounted parallel with a longitudinal axis of the balloon and is utilized for determining longitudinal strain in the balloon and correlating the determined strain to a longitudinal growth of the balloon.

15. The method of claim 10, wherein the fiber distal portion is wrapped at least partially helically around the balloon and is utilized for determining strain in the balloon and correlating the determined strain to a circumferential growth of the balloon.

16. The method of claim 10, wherein the distal portion of the optical fiber helically wraps around the balloon and includes multiple FBG sensors.

17. The method of claim 10, further comprising:
a semiconductor chip coupled to a hub of the catheter, wherein the semiconductor chip includes a strain parameter of the balloon that serves as an input for the wavelength detector.

* * * * *